(12) United States Patent
Kim et al.

(10) Patent No.: US 12,062,450 B2
(45) Date of Patent: Aug. 13, 2024

(54) DISEASE DIAGNOSIS SYSTEM AND METHOD FOR PERFORMING SEGMENTATION BY USING NEURAL NETWORK AND UNLOCALIZED BLOCK

(71) Applicant: DEEP BIO INC., Seoul (KR)

(72) Inventors: Sun Woo Kim, Seongnam-si (KR); Joon Young Cho, Seoul (KR); Sang Hun Lee, Seoul (KR)

(73) Assignee: DEEP BIO INC., Seoul (KR)

( * ) Notice: Subject to any disclaimer, the term of this patent is extended or adjusted under 35 U.S.C. 154(b) by 327 days.

(21) Appl. No.: 17/626,806

(22) PCT Filed: Jul. 10, 2020

(86) PCT No.: PCT/KR2020/009096
§ 371 (c)(1),
(2) Date: Jan. 12, 2022

(87) PCT Pub. No.: WO2021/010671
PCT Pub. Date: Jan. 21, 2021

(65) Prior Publication Data
US 2022/0301712 A1    Sep. 22, 2022

(30) Foreign Application Priority Data
Jul. 13, 2019   (KR) .......................... 10-2019-0084814

(51) Int. Cl.
*G16H 50/20*    (2018.01)
*G06F 18/24*    (2023.01)
(Continued)

(52) U.S. Cl.
CPC ............. *G16H 50/20* (2018.01); *G06F 18/24* (2023.01); *G06T 7/0012* (2013.01); *G06T 7/11* (2017.01);
(Continued)

(58) Field of Classification Search
CPC ........ G16H 50/20; G16H 30/20; G16H 30/40; G16T 7/11; G06F 18/24; G06T 7/0012; G06V 10/70
(Continued)

(56) References Cited

U.S. PATENT DOCUMENTS 11,074,686 B2 *  7/2021  Kim ....................... G16H 30/40
11,210,787 B1 * 12/2021  Godrich ................. G16H 50/20
(Continued)

FOREIGN PATENT DOCUMENTS

CN     109919961       6/2019
JP     2021-535472    12/2021
(Continued)

OTHER PUBLICATIONS

Hongzhen Wang, et al., "Gated Convolutional Neural Network for Semantic Segmentation in High-Resolution Images", Remote Sensing, May 5, 2017, vol. 9, p. 446, Switzerland.
(Continued)

*Primary Examiner* — William D Titcomb
(74) *Attorney, Agent, or Firm* — PnK IP LLC

(57) ABSTRACT

A disease diagnosis system uses a slide of a biological image and the neural network, the disease diagnosis system including a patch-level segmentation neural network that receives, for each predetermined patch in which the slide is divided into a predetermined size, the patch as an input layer so as to specify the area in which the disease in the patch exists, wherein the patch-level segmentation neural network comprises: a patch-level classification neural network, which receives the patch as an input layer so as to output a patch-level classification result about whether the disease exists in the patch; and a patch-level segmentation architecture, which receives a feature map generated in each of two or more feature map extraction layers from among hidden
(Continued)

layers included in the patch-level classification neural network, so as to specify the area in which the disease in the patch exists.

12 Claims, 11 Drawing Sheets

(51) Int. Cl.
  *G06T 7/00* (2017.01)
  *G06T 7/11* (2017.01)
  *G16H 30/20* (2018.01)
  *G16H 30/40* (2018.01)
  *G06V 10/70* (2022.01)

(52) U.S. Cl.
  CPC ............. *G16H 30/20* (2018.01); *G16H 30/40* (2018.01); *G06V 10/70* (2022.01)

(58) Field of Classification Search
  USPC ........................................... 382/156
  See application file for complete search history.

(56) References Cited

U.S. PATENT DOCUMENTS

| | | | |
|---|---|---|---|
| 11,373,304 B2* | 6/2022 | Katscher | G06V 20/698 |
| 11,798,686 B2* | 10/2023 | Kwak | G16H 30/40 |
| 2012/0010528 A1* | 1/2012 | Donovan | G06T 7/194 |
| | | | 382/128 |
| 2013/0094704 A1* | 4/2013 | Hamadeh | G06N 3/02 |
| | | | 382/103 |
| 2016/0086078 A1 | 3/2016 | Ji et al. | |
| 2017/0193175 A1* | 7/2017 | Madabhushi | G06V 10/82 |
| 2018/0075628 A1* | 3/2018 | Teare | G06F 18/24143 |
| 2018/0232883 A1* | 8/2018 | Sethi | G16H 30/40 |
| 2020/0090381 A1* | 3/2020 | Teare | G16H 50/30 |
| 2020/0226368 A1* | 7/2020 | Bakalo | G06N 3/045 |
| 2020/0372635 A1* | 11/2020 | Veidman | G06T 7/0012 |
| 2020/0381122 A1* | 12/2020 | Godrich | G16B 40/20 |
| 2021/0193323 A1* | 6/2021 | Jain | G16H 50/70 |
| 2021/0224268 A1* | 7/2021 | Kim | G16H 10/60 |
| 2021/0248745 A1* | 8/2021 | Cho | G16H 50/20 |
| 2021/0249101 A1* | 8/2021 | Jain | G16B 40/30 |
| 2021/0295509 A1* | 9/2021 | Lee | G16H 50/20 |
| 2021/0304405 A1* | 9/2021 | Cho | G16H 30/40 |
| 2021/0327534 A1* | 10/2021 | Nicula | G16B 20/00 |
| 2022/0076410 A1* | 3/2022 | Georgescu | G06V 20/698 |

FOREIGN PATENT DOCUMENTS

| | | |
|---|---|---|
| KR | 10-2016-0034814 | 3/2016 |
| KR | 10-2018-0066983 | 6/2018 |
| KR | 101889725 | 8/2018 |

OTHER PUBLICATIONS

Xiaolong Wang, et al., "Non-local Neural Networks", Proceedings of the IEEE conference on computer vision and pattern recognition, 2018, pp. 7794-7803.

Wang, D., Khosla, A., Gargeya, R., Irshad, H., & Beck, A. H. (2016). Deep Learning for Identifying Metastatic Breast Cancer. arXiv: 1606.05718v1 [q-bio.QM].

* cited by examiner

DISEASE DIAGNOSIS SYSTEM AND METHOD FOR PERFORMING SEGMENTATION BY USING NEURAL NETWORK AND UNLOCALIZED BLOCK

CROSS REFERENCE TO RELATED APPLICATION

This application is a National Stage Entry of International Application No. PCT/KR2020/009096, filed on Jul. 10, 2020, and claims priority from and the benefit of Korean Patent Application No. 10-2019-0084814, filed on Jul. 13, 2019, each of which is hereby incorporated by reference for all purposes as if fully set forth herein.

BACKGROUND

Field

Embodiments of the invention relate generally to a disease diagnosis system and method using a neural network. In specific, the present invention relates to a disease diagnosis system and method that is capable of performing learning through a neural network to allow a disease area in a biological tissue image to be segmented using the learning performed by the neural network and a non-local block.

Discussion of the Background

One of main works executed in pathology interprets a patient's bio-image and performs a diagnosis for determining his or her conditions or symptoms of a specific disease. The diagnosis is made depending upon the experiences and knowledge of a medical professional working for a long time.

With the development of machine learning, recently, tries to automatically perform works for recognizing or sorting images through a computer system have been actively made. In specific, tries to automatically perform diagnoses, not by the medical professional, but by deep learning using a neural network (for example, a convolution neural network (CNN)) that is a class of machine learning.

The diagnosis performed through the deep learning using the neural network (for example, CNN) does not simply automate the experiences and knowledge of the medical professional, but finds characteristic elements through learning to extract desired solutions from the characteristic elements. Accordingly, the characteristics of disease factors, which are not recognized even by the medical professional, can be found from the bio-image.

Generally, a disease diagnosis through the neural network using the bio-image is performed using pieces of the bio-image, that is, patches or tiles. That is, annotation for the tiles is performed by the medical professional to determine a state of a specific disease (for example, whether a cancer is expressed) and the tiles after the annotation are used as training data to allow the neural network to learn. In this case, the convolution neural network may be used as the neural network.

In the above-mentioned method, however, the neural network performing learning determines the disease states of the tiles just from the image characteristics of the corresponding tiles, but when the state of a specific biological tissue for a specific disease is determined, actually, there are some cases in which the state of the specific biological tissue and the state (that is, shape, existence of specific patterns, and the like) of the adjacent tissues to the specific biological tissue have to be all considered. However, the above-mentioned conventional method is not proper for such cases.

In the case where it is determined whether a disease is expressed by patch according to diagnosis results in a unit of patch, further, the diagnosis result on which the disease is expressed on a specific patch is produced, but there is a probability that it will be determined that the disease is not expressed in a wide range. Based on the diagnosis results by patch, accordingly, it is necessary to separately determine whether the disease is expressed on an entire slide including the corresponding patches.

If the patch unit diagnosis results are immediately visualized after determining (classification by patch) whether the disease is expressed by patch according to the patch unit diagnosis results, further, even portions that do not correspond to the tissue may be visualized undesirably. Accordingly, there is a need to perform segmentation through which a disease area is segmented from the patch to clearly recognize the tissue portion diagnosed as the disease.

In the disease diagnosis through the neural network using the bio-image, further, a three-dimensional prostate is diagnosed from a two-dimensional image, and accordingly, a tangential problem may occur. For example, when glands having similar shapes to one another are found on different slides, pathologists make diagnosis results (for example, image/audio, Gleason score of 3 or 4) after considering the adjacent glands. That is, the pathologists normally make their diagnosis after considering the adjacent tissue, but generally, existing deep learning networks do not reflect the adjacent tissue state on their diagnosis.

Patent Document Korean Patent Application No. 10-2016-0034814 entitled 'Client device with neural network and system having same'

The above information disclosed in this Background section is only for understanding of the background of the inventive concepts, and, therefore, it may contain information that does not constitute prior art.

SUMMARY

Accordingly, the present invention has been made in view of the above-mentioned problems occurring in the related art, and it is an object of the present invention to provide a disease diagnosis system and method using a neural network that is capable of determining whether a disease is expressed on a specific patch and segmenting a disease area on the specific patch from an entire area thereof. In specific, it is an object of the present invention to provide a disease diagnosis system and method that is configured to add a segmentation sub-architecture to a classification neural network architecture determining whether a disease exists on patches, thereby efficiently performing segmentation for detecting a disease area on which the disease exists.

It is another object of the present invention to provide a disease diagnosis system and method using a neural network that is capable of making use of a specific tile and the adjacent tiles thereto so as to determine a disease state (for example, expression of disease or index indicating the disease state) of the specific patch, thereby enhancing a degree of accuracy in a diagnosis result.

It is yet another object of the present invention to provide a disease diagnosis system and method that is capable of effectively diagnosing whether a disease is expressed on a wide-ranging biological tissue including patches, not based on only diagnosis results by patch, with high accuracy, while utilizing the diagnosis results by patch.

To accomplish the above-mentioned objects, according to an aspect of the present invention, there is provided a disease diagnosis system implemented in a system having a processor and a storage device storing a neural network to perform a disease diagnosis using a slide as a bio-image and the neural network, the disease diagnosis system including: a patch-level segmentation neural net work for receiving, given patches made by dividing the slide into a predetermined size, as input layers, to specify a disease area in which a given disease exists among the patches, wherein the patch-level segmentation neural network may include: a patch-level classification neural network for receiving the patches as the input layers to produce a patch-level classification result indicating whether the disease exists on the patches; and a patch-level segmentation architecture for receiving feature maps produced from two or more feature map extraction layers among hidden layers included in the patch-level classification neural network to thus specify the disease area among the patches, and the patch-level segmentation architecture may include: a non-local correlation calculation sub-architecture having non-local correlation calculation nodes corresponding to the two or more feature map extraction layers, respectively, the non-local correlation calculation nodes performing non-local correlation calculation processes for the feature maps received from the feature map extraction layers corresponding thereto, the correlation calculation processes being performed by convolution execution processes, non-local block execution processes, or parallel processes of the convolution and the non-local block; and a segmentation sub-architecture for specifying the disease area among the patches, based on the results produced from the non-local correlation calculation sub-architecture.

According to the present invention, the segmentation sub-architecture produces a mask corresponding to the disease area among the patches through convolution and concatenation for the results produced from the non-local correlation calculation sub-architecture.

According to the present invention, the feature map extraction layers of the patch-level classification neural network may include a low feature map extraction layer, a middle feature map extraction layer, and a high feature map extraction layer, and the non-local correlation calculation nodes of the non-local correlation calculation sub-architecture may include a low-level non-local correlation calculation node for performing the convolution process for the feature map received from the low feature map extraction layer to produce a first convolution result, a middle-level non-local correlation calculation node for performing the non-local block and convolution processes in parallel for the feature map received from the middle feature map extraction layer to produce a first non-local result and a second convolution result, and a high-level non-local correlation calculation node for performing the non-local block for the feature map received from the high feature map extraction layer to produce a second non-local result.

According to the present invention, the segmentation sub-architecture concatenates the first non-local result, the second convolution result, and an upscaling result of the second non-local block to thus produce a first middle result, concatenates a second middle result produced by convoluting and upscaling the first middle result and the first convolution result to thus produce a third middle result, and performs the convolution for the third middle result to produce the mask corresponding to the disease area among the patches.

According to the present invention, the disease diagnosis system may further include a slide diagnosis engine for marking the patches classified as disease patches according to the patch level classification results for the patches of the slide to thus produce a slide-level diagnosis result indicting whether the disease exists on the slide according to the marking results.

According to the present invention, the disease is a prostate cancer.

To accomplish the above-mentioned objects, according to another aspect of the present invention, there is provided a disease diagnosis method conducted in a system having a processor and a storage device storing a neural network to perform a disease diagnosis using a slide as a bio-image and the neural network, the disease diagnosis method including the step of: receiving, given patches made by dividing the slide into a predetermined size, as input layers, to specify a disease area in which a given disease exists among the patches, through a patch-level segmentation neural network, wherein the patch-level segmentation neural network may include: a patch-level classification neural network for receiving the patches as the input layers to produce a patch-level classification result indicating whether the disease exists on the patches; and a patch-level segmentation architecture for receiving feature maps produced from two or more feature map extraction layers among hidden layers included in the patch-level classification neural network to thus specify the disease area among the patches, and the patch-level segmentation architecture may include: a non-local correlation calculation sub-architecture having non-local correlation calculation nodes corresponding to the two or more feature map extraction layers, respectively, the non-local correlation calculation nodes performing non-local correlation calculation processes for the feature maps received from the feature map extraction layers corresponding thereto, the correlation calculation processes being performed by convolution, non-local block, or a parallel process of convolution and non-local block; and a segmentation sub-architecture for specifying the disease area among the patches, based on the results produced from the non-local correlation calculation sub-architecture.

According to the present invention, the disease diagnosis method may further include the step of: marking the patches classified as disease patches according to the patch level classification results for the patches of the slide to thus produce a slide-level diagnosis result indicting whether the disease exists on the slide according to the marking results, through the system.

To accomplish the above-mentioned objects, according to yet another aspect of the present invention, there is provided a computer program installed in a data processing device and recorded in a medium for implementing the above-mentioned method.

According to the technical features of the present invention, the disease diagnosis system and method using a neural network can perform patch-level classification for determining whether a disease is expressed by patch and patch-level segmentation for segmenting a disease area on a specific patch, thereby providing a diagnosis more accurately on a pathologic view.

According to the technical features of the present invention, further, the disease diagnosis system and method can be configured to have a neural network adapted to determine a disease state of a specific patch in consideration of macro patches with the adjacent patches to the specific patch as well as the specific patch, while performing a diagnosis for the specific patch, thereby providing a high degree of accuracy in the diagnosis.

According to the technical features of the present invention, in addition, the disease diagnosis system and method using a neural network can determine whether a disease is expressed on a slide having patches using clusters and the features of the clusters, again so as to solve a problem occurring in the case where it is determined that the disease is expressed on the slide with the patches only using diagnosis results by patch, thereby effectively performing a diagnosis with high accuracy.

Additional features of the inventive concepts will be set forth in the description which follows, and in part will be apparent from the description, or may be learned by practice of the inventive concepts.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

Now, explanations of drawings are briefly given so as to allow the drawings mentioned in the description to be understood well.

FIG. 8b is a diagram showing an example of a deep neural network of FIG. 8a.

DETAILED DESCRIPTION

Figure 1:
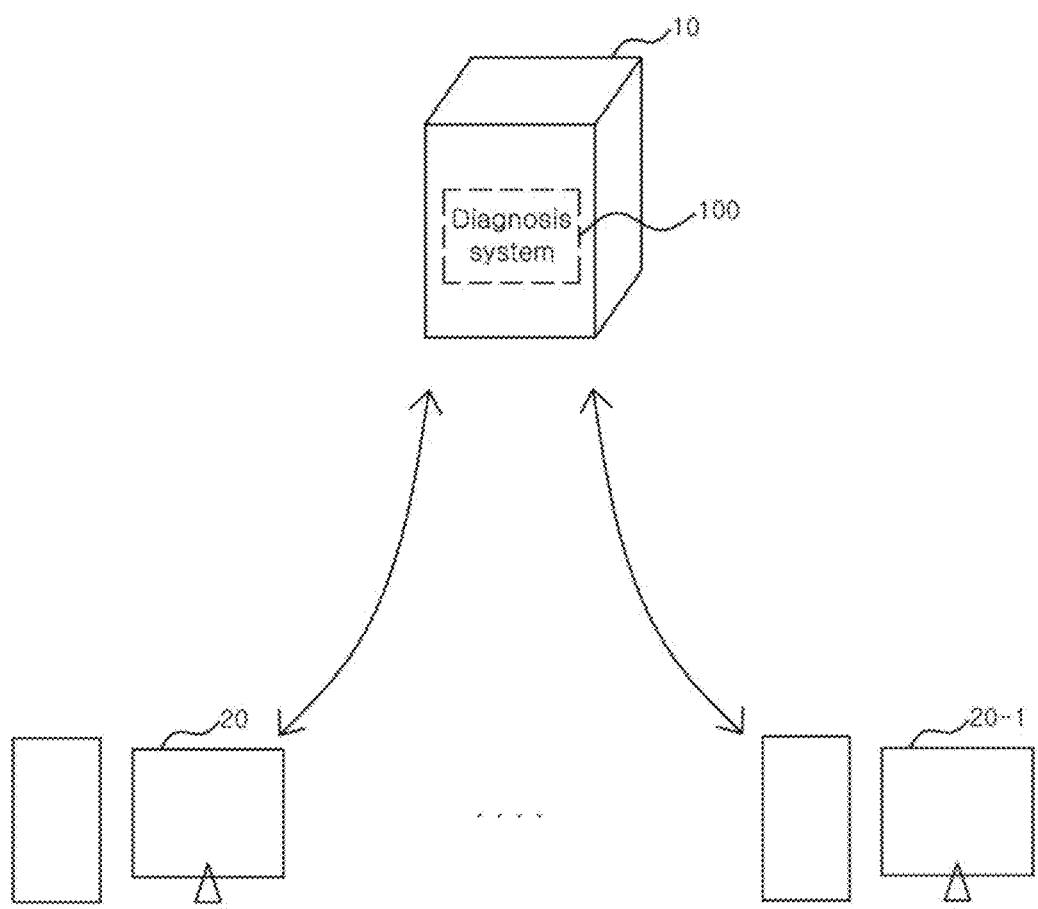
FIG. 1 is a block diagram showing a schematic configuration of a disease diagnosis system performing segmentation using a neural network and a non-local block according to the present invention.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

The present invention is disclosed with reference to the attached drawings wherein the corresponding parts in the embodiments of the present invention are indicated by corresponding reference numerals.

FIG. 1 is a block diagram showing a schematic configuration of a disease diagnosis system (hereinafter referred to as 'diagnosis system') performing segmentation using a neural network and a non-local block according to the present invention.

Referring to FIG. 1, a diagnosis system 100 according to the present invention is installed in a given server 10 to implement the technical features of the present invention. The server 10 means a data processing device having operation capability with which the technical features of the present invention are implemented, and generally, a data processing device to which a client is accessible through a network and a device capable of performing specific services, such as a personal computer, a portable terminal, and the like may be defined as the server, which will be easily understood by a person having ordinary skill in the art.

Figure 2:
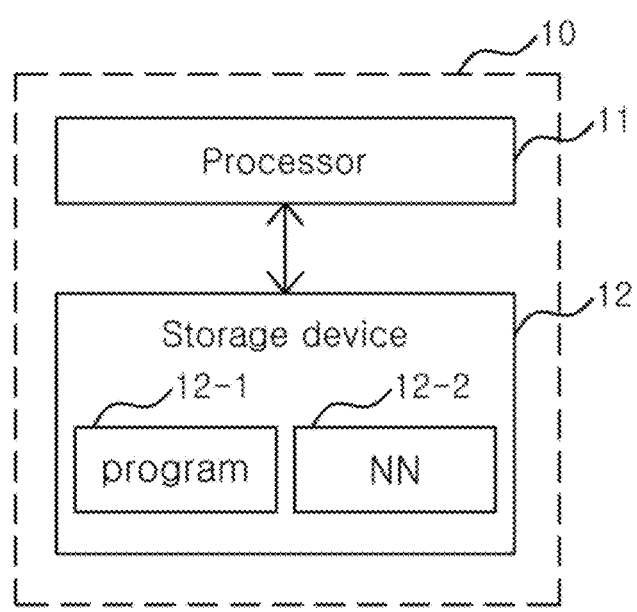
FIG. 2 is a block diagram showing a hardware configuration of the disease diagnosis system using the neural network according to the present invention.

As shown in FIG. 2, the server 10 includes a processor 11 and a storage device 12. The processor 11 means an operation device for driving a program 12-1 for implementing the technical features of the present invention, and the processor 11 performs a diagnosis using the program 12-1 and a neural network 12-2 defined by the technical features of the present invention. The neural network 12-2 includes a patch-level segmentation neural network for performing a patch-level diagnosis, which will be discussed later. Further, the patch-level segmentation neural network performs patch-level segmentation for specifying a disease area among patches.

According to embodiments of the present invention, the neural network 12-2 further includes a neural network for performing a slide-level diagnosis. The slide-level diagnosis may be performed by various machining learning as well as the neural network. According to the technical features of the present invention, a diagnosis engine for performing the slide-level diagnosis is used as a well known XGBoost, but of course, the diagnosis engine may be provided in accordance with various machine learning techniques. The diagnosis engine is of course stored in the storage device 12.

As shown in FIG. 2, the server 10 includes the processor 11 and the storage device 12. The processor 11 means an operation device for driving the program 12-1 for implementing the technical features of the present invention, and the processor 11 performs a diagnosis using the program 12-1 and the neural network 12-2 defined by the technical features of the present invention.

The neural network 12-2 includes the patch-level segmentation neural network for performing patch-level diagnosis, which will be discussed later. The patch-level segmentation neural network for performing patch-level diagnosis determines whether a disease exists on patches as divided portions of a slide. Further, the patch-level segmentation neural network for performing patch-level diagnosis performs segmentation for specifying a disease area on the patches, and hereinafter, the patch-level segmentation neural network for performing patch-level diagnosis is simply called the patch-level segmentation neural network.

According to embodiments of the present invention, the neural network 12-2 further includes the neural network for performing a slide-level diagnosis. The slide-level diagnosis may be performed by various machining learning as well as the neural network. According to the technical features of the present invention, a diagnosis engine for performing the slide-level diagnosis is used as a well known XGBoost, but of course, the diagnosis engine may be provided in accordance with various machine learning techniques. The diagnosis engine is of course stored in the storage device 12.

The storage device 12 indicates a data storage means for storing the program 12-1, the neural network 12-2, and/or the diagnosis engine for performing the slide-level diagnosis, and according to embodiments of the present invention, the storage device 12 indicate a plurality of storage means. Further, the storage device 2 includes a main memory included in the server 10 as well as a temporary storage device or memory included in the processor 11.

The diagnosis system 100 is provided as one physical device in FIG. 1 or 2, but if necessary, a plurality of physical devices are coupled organically to one another and thus provided as the diagnosis system 100 according to the technical features of the present invention, which will be easily understood by a person having ordinary skill in the art.

In the description, a process of performing a diagnosis through the diagnosis system 100 is a series of processes for receiving patches as a whole or portion of a bio-image expressing a biological tissue, that is, a slide to thus produce output data defined in the present invention.

According to the present invention, the diagnosis system 100 performs a two-phase diagnosis. A first phase is a process of performing a patch-level diagnosis, and in this process, the diagnosis system 100 receives inputs from the patches of the slide, produces results indicating whether a disease is expressed on the patches, and/or specifies a disease area on the corresponding patch. To do this, of course, learning through the neural network is implemented.

The second phase is a process of producing a result indicating whether the disease is expressed on the slide through the diagnosis result of the first phase. The process is performed by the neural network or given machine learning.

In specific, even though the disease is expressed on some patches according to the diagnosis results by patch, there is a possibility that it will be determined that the disease is not expressed on the biological tissue corresponding to the entire slide including the corresponding patches. For example, the patches on which the disease is expressed through the determination may be irregularly dispersed in the slide, the number of such patches may be small, or a density of such patches may be low. Like this, in this case, it is determined whether the disease is expressed on the slide in accordance with the physical features (for example, positions, sizes, and density) of the patches on which the disease is expressed. Accordingly, the second phase determines whether the disease is expressed on the slide, based on the diagnosis results by patch and the physical features of the patches (on which the disease is expressed) determined according to the diagnosis results, thereby effectively performing the diagnosis with a high degree of accuracy.

According to the technical features of the present invention, further, the neural network for performing the patch-level diagnosis can perform the diagnosis using only the corresponding patch as well as using the adjacent patches to the corresponding patch. The technical features of the present invention are disclosed in detail in Korean Patent Application No. 10-2016-0168176 filed by the same applicant as the present invention and entitled 'Disease diagnosis system and method using neural network' (hereinafter referred to 'Prior art'). Accordingly, when compared to the diagnosis performed in consideration of a local area, that is, only the area corresponding to the patch, the diagnosis performed in consideration of even the adjacent areas to the patch as well as the corresponding patch can enhance a degree of accuracy in the diagnosis. According to the technical features of the present invention, as the adjacent patches to a specific patch as well as the physical features of the patches in the entire slide, such as positions of patches, patch density, sizes of clusters, and the like are additionally considered, it is more accurately determined whether a disease exists on the slide. The Prior art is provided as a reference of the present invention, the contents of which are provided as described in the present invention.

Figure 6:
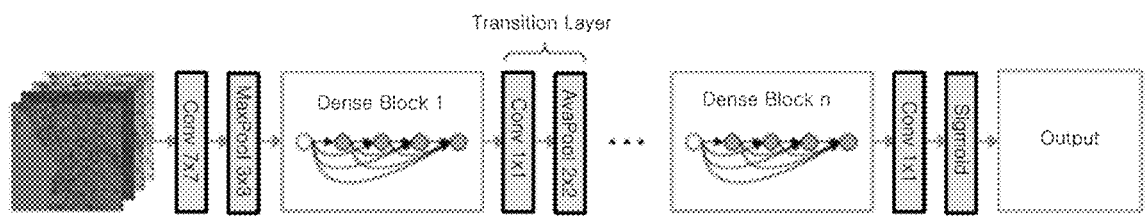
FIG. 6 is a schematic view showing another example in the configuration of the patch-level classification neural network according to the present invention.

Of course, according to another embodiment of the present invention, unlike the Prior art in which a micro network and a macro network, that is, a two-way neural network is used, the present invention makes use of a one-way network. For example, the neural network according to the present invention is provided as shown in FIG. 6.

Only if a neural network receives the patches and produces a result indicating whether the disease is expressed on the received patches, it can be used as the neural network according to the present invention. In this case, the neural network learns to receive a gray channel as an input value, in addition to an original input value (for example, three RGB channels) and perform the diagnosis.

Further, the state information produced from the neural network performing the patch-level diagnosis indicates the information of a probability indicating whether a specific disease (for example, a specific cancer) is expressed on the tissue corresponding to the patch. If the probability greater than a specific reference value (threshold) appears, the neural network determines the patch as the patch on which the specific disease (for example, a prostate cancer) is expressed.

Of course, the state information produced from the neural network may be information indicating whether the specific disease is expressed, as disclosed in the Prior art, as well as information (or a probability corresponding to the progression of the specific disease) indicating the progression of the specific disease. For example, if the technical features of the present invention are applied to the prostate cancer, Gleason pattern or Gleason scores as the indexes indicating the progression of the prostate cancer may be included in the state information produced from the neural network. For example, Gleason scores have values of 2 to 5, and the bigger the number is, the higher the expressed degree of the prostate cancer is. Accordingly, the state information may indicate a probability that the biological tissue corresponding to the patch as a diagnosis subject corresponds to the specific value (for example, 3, 4, or 5) of the Gleason score.

The state information may include a plurality of pieces of information. For example, a first piece of state information indicates a probability having the Gleason score of 3, a second piece of state information indicates a probability having the Gleason score of 4, and a third piece of state information indicates a probability having the Gleason score of 5. All state channels corresponding to the first piece of state information, the second piece of state information, and the third piece of state information may be defined on an output layer. According to embodiments of the present invention, the state information indicating a probability that the Gleason score will have a given value (for example, 3 to 5, 4 to 5, etc.) may be defined. That is, one piece of state information may correspond to a plurality of indexes indicating the progression of the disease.

In this case, if the state information having the Gleason score greater than or equal to 3 is greater than or equal to a given threshold, the neural network determines the patch as a patch on which the disease is expressed.

Further, the threshold used by the neural network may be freely set. According to the present invention, a plurality of thresholds may be used. According to the thresholds, accordingly, a specific patch is determined as a patch on which a disease is expressed or as a normal patch.

According to the technical features of the present invention, the plurality of thresholds may be used by the neural network, and in this case, the patch on which the disease is diagnosed may be varied according to the thresholds. Accordingly, the arrangement of the patch on the slide may be also varied according to the thresholds. Therefore, the accuracy of the diagnosis result on the slide may be changed according to the thresholds.

According to the technical features of the present invention, a slide diagnosis engine can perform a slide diagnosis, while considering the physical features of the patches on which the disease is diagnosed on the slide according to the respective thresholds, which will be discussed later. The technical features of the present invention will be described later.

If the diagnosis system 100 is included in the given server 10, the diagnosis system 100 performs communication with at least one or more clients (for example, 20 and 20-1) accessible to the server 10. In this case, the clients (for example, 20 and 20-1) transmit bio-images to the diagnosis system 100, and the diagnosis system 100 performs the diagnoses for the bio-images received according to the technical features of the present invention. Further, the diagnosis system 100 transmits diagnosis results to the clients (for example, 20 and 20-1).

The diagnosis system 100 performs the patch-level diagnosis using the neural network according to the technical features of the present invention. Of course, a process of allowing the neural network to learn to perform the patch-level diagnosis is first executed.

As mentioned above, further, the slide-level diagnosis is performed by means of a given neural network.

Accordingly, the diagnosis system 100 according to the present invention may be provided as a system that receives a neural network performing learning and a program for performing a diagnosis using the neural network from the outside to perform the diagnosis, and further, the diagnosis system 100 may be provided as a system for allowing the neural network to learn. Moreover, the diagnosis system 100 may be provided as a dedicated device manufactured to implement the technical features of the present invention, not a general data processing device, and in this case, the diagnosis system 100 may further include a means for scanning bio-images.

The neural network does not consider only the image of a specific patch to perform the diagnosis for the specific patch, as mentioned in the Prior art, and considers even at least one patch adjacent to the specific patch to thus perform the diagnosis. So as to execute the diagnosis for the biological tissue corresponding to the specific patch, the diagnosis of a disease has to be performed in consideration of the state of the biological tissue as well as the state of the adjacent tissue to the biological tissue, and according to the present invention, accordingly, it is possible that the accuracy of the diagnosis for the specific patch can be significantly improved. If the bio-image is divided into a plurality of patches, further, the diagnosis result may be robustly influenced according to the division way of the patches or the positions of the divided areas on the biological tissue.

As mentioned above, of course, the neural network may not have the features of the Prior art, but even in any case, the neural network may learn to perform diagnoses by patch.

In this case, the neural network receives additional channels for the pixels included in the patches, as input values, unlike the Prior art. The additional channels are gray values of the respective pixels. Accordingly, the neural network receives inputs by patch and further receives the three original value channels (for example, three RGB channels) included in the patches and the gray channels as the additional channels.

In the case where the color of the bio-image is changed due to reasons (for example, the characteristics of a diagnosis agency, stain kits, etc.) having no relation with the image characteristics related to the disease, the input of the additional channels has robust effectiveness. Of course, if only the gray channels are used, without any use of the original values, undesirably, important information may not be transmitted to the learning when the image characteristics related to the disease are reflectedly displayed onto colors, and accordingly, such a problem may be solved.

Figure 3:
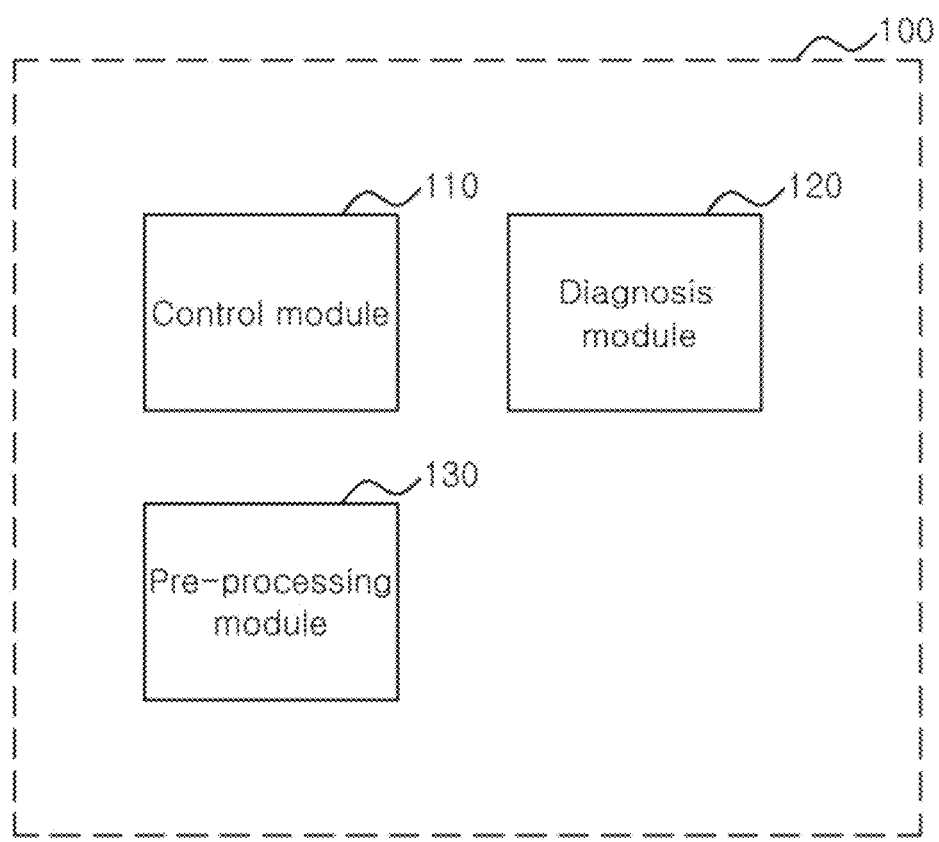
FIG. 3 is a block diagram showing a logical configuration of the disease diagnosis system using the neural network according to the present invention.

To implement the technical features of the present invention, the diagnosis system 100 has a logical configuration as shown in FIG. 3.

FIG. 3 is a block diagram showing a logical configuration of the disease diagnosis system using the neural network according to the present invention.

Referring to FIG. 3, the diagnosis system 100 includes a control module 110 and a diagnosis module 120 in which the neural network and/or the slide diagnosis engine are stored. Further, the diagnosis system 100 includes a pre-processing module 130. According to the present invention, some of the above-mentioned components may not be necessarily required, and the diagnosis system 100 according to the present invention may further include a larger number of components. For example, the diagnosis system 100 may further include a communication module (not shown) for performing communication with the clients (for example, 20 and 20-1).

The diagnosis system 100 means a logical configuration having hardware resource and/or software required to implement the technical features of the present invention and does not mean one physical component or device. That is, the diagnosis system 100 means a logical combination of hardware and/or software required to implement the technical features of the present invention, and so as to implement the technical features of the present invention, if necessary, the diagnosis system 100 may be provided as a set of logical components installed on separated devices from each other to execute respective functions. Further, the diagnosis system 100 may be provided as a set of components operating separately by function or role to implement the technical features of the present invention. For example, the control module 110, the diagnosis module 120, and/or the pre-processing module 130 may be located on different physical devices from one another, and otherwise, they may be located on the same physical device as one another. According to the present invention, further, combinations of software and/or hardware constituting the control module 110, the diagnosis module 120, and/or the pre-processing module 130, respectively may be located on different physical devices from one another, and the components located on the different physical devices may be organically coupled to constitute the respective modules.

Further, a term 'module' used in the description means a functional and structural combination of hardware for implementing the technical features of the present invention and software for driving the hardware. For example, the module means given codes or a logical unit of a hardware resource through which the given codes are implemented, and the module does not necessarily mean codes connected physically to one another or one kind of hardware, which is easily understood by a person having ordinary skill in the art.

The control module 110 controls other components (for example, the diagnosis module 120 and/or the pre-processing module 130) in the diagnosis system 100 to implement the technical features of the present invention.

Further, the control module 110 performs the diagnosis according to the technical features of the present invention, while using the neural network and/or the slide diagnosis engine stored in the diagnosis module 120.

The control module 110 receives input data, that is, inputs by patch from the patch-level neural network, that is, the neural network stored in the diagnosis module 120 to perform learning. Further, the control module 110 executes operations defined by the neural network to produce output data, that is, feature values corresponding to disease expression probabilities' on the patches. According to the present invention, further, the control module 110 specifies the disease area on which the disease is expressed among the patches. Moreover, the control module 110 produces a result indicating whether the disease is expressed on the corresponding patch, depending on whether the feature values are given thresholds.

The diagnosis module 120 includes the patch diagnosis engine for performing the patch-level diagnosis and the slide diagnosis engine for performing the slide-level diagnosis.

As mentioned above, the patch diagnosis engine is implemented through the deep learning-based neural network according to the technical features of the present invention. The slide diagnosis engine is implemented through the deep learning-based neural network, and otherwise, the slide diagnosis engine may be used through a given machine learning (for example, XGBoost) engine, not the neural network.

The neural network means a set of information indicating a series of design facts for defining it. According to the present invention, the neural network is a convolution neural network.

As well known, the convolution neural network includes an input layer, a plurality of hidden layers, and an output layer. Each hidden layer includes a convolution layer and a pooling layer (or sub-sampling layer).

The convolution neural network is defined by functions, filters, strides, and weight factors that define the respective layers. Further, the output layer is defined as a fully connected feedforward layer.

The design factors of the layers constituting the convolution neural network are widely known. For example, the design factors may include the number of layers included in the plurality of layers and known functions for convolution functions, pooling functions, and activation functions for defining the plurality of layers, and otherwise, functions separately defined to implement the technical features of the present invention may be used.

As mentioned above, the neural network for performing the patch-level diagnosis may be provided as the patch-level segmentation neural network that determines whether a disease exists on the patch and performs segmentation for specifying a disease area of the corresponding patch.

According to the present invention, the patch-level segmentation neural network is provided in a form of a combination of a neural network (that is, a patch-level classification neural network as will be discussed below) for performing classification for determining whether a disease exists on the patch and a separate architecture for segmentation. A structure of the patch-level segmentation neural network is shown in FIG. 4.

Figure 4:
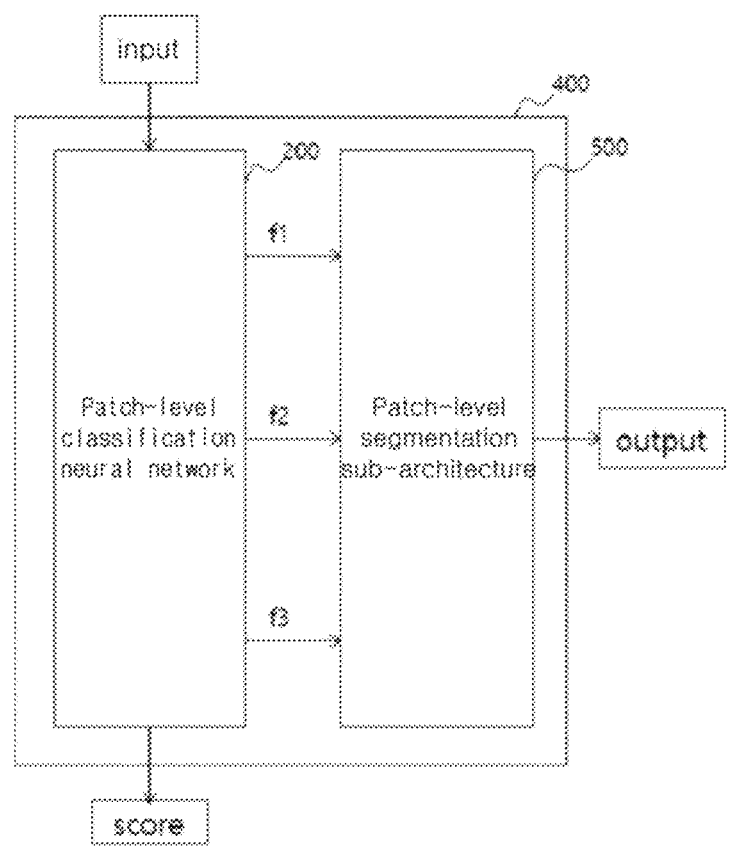
FIG. 4 is a schematic view showing an overall configuration of a patch-level classification neural network according to the present invention.

FIG. 4 is a schematic view showing an overall configuration of a patch-level classification neural network according to the present invention.

As shown in FIG. 4, a patch-level segmentation neural network 400 according to the present invention includes a patch-level classification neural network 200 and a patch-level segmentation architecture 500.

The patch-level classification neural network 200 receives patches prepared by dividing a slide, as the input layer, to produce patch-level classification results (for example, scores as shown in FIG. 4) indicating whether the disease exists on the patches. This process is called classification, and in the classification process, the patch-level classification neural network 200 produces features for the inputs (that is, patches) as intermediate products from some hidden layers included therein. In specific, in the case where matrixes with more than two dimensions are received, the produced features are in the form of two-dimensional matrixes, and accordingly, the features may be called feature maps. Hereinafter, the layers producing the feature maps among the hidden layers included in the patch-level classification neural network 200 are called feature map extraction layers.

Further, the patch-level segmentation architecture 500 receives the feature maps (for example, f1, f2, and f3 as shown in FIG. 4) produced from two or more feature map extraction layers among the hidden layers included in the patch-level classification neural network 200 and specifies the disease area among the patches.

FIG. 4 shows an example in which the patch-level classification neural network 200 produces three feature maps (low feature map of f1, middle feature map of f2, and high feature map of f3) in the process of the classification, but according to embodiments of the present invention, of course, the number of feature maps produced may be increased or decreased.

According to embodiments of the present invention, further, a well known DenseNet may be used as the patch-level classification neural network 200 for performing the patch-level classification, and in this case, as disclosed in the Prior art, the patch-level classification neural network 200 may be designed to consider a specific patch as a diagnosis subject as well as patches adjacent to the specific patch. In addition thereto, various neural networks may be used as the patch-level classification neural network 200, and in any case, the patch-level classification neural network 200 receives the specific patch as an input and produces the feature value corresponding to the disease expression probability of the specific patch.

Figure 5A:
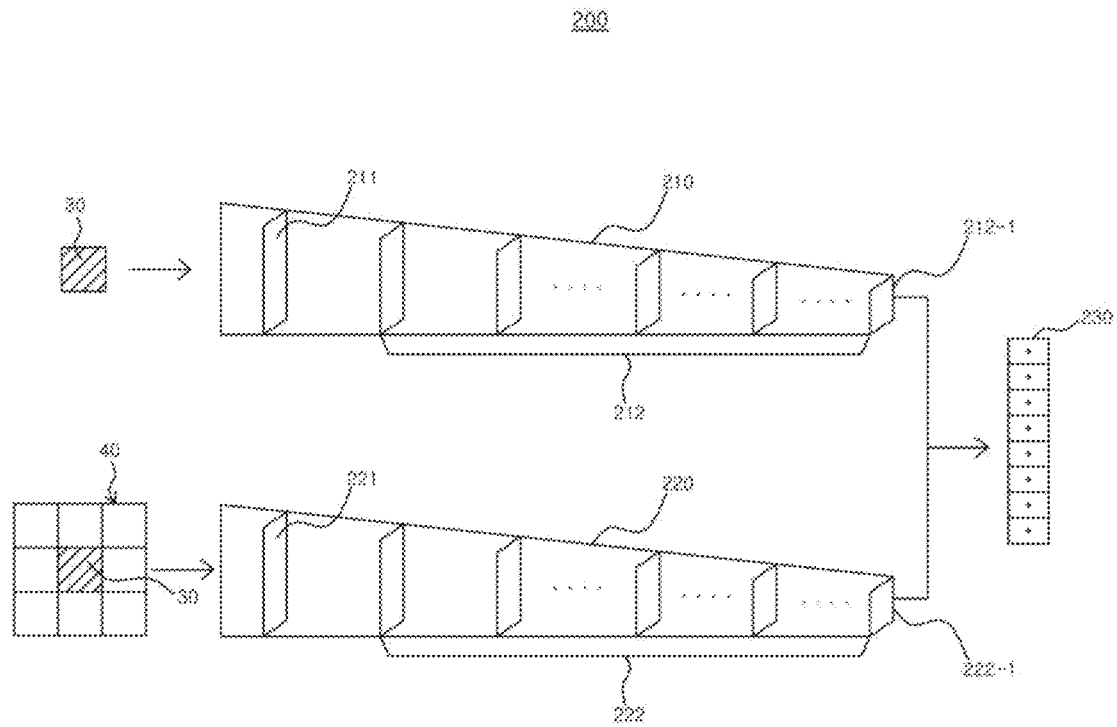
FIGS. 5a and 5b are schematic views showing the configuration of the patch-level classification neural network according to the present invention.
Figure 5B:
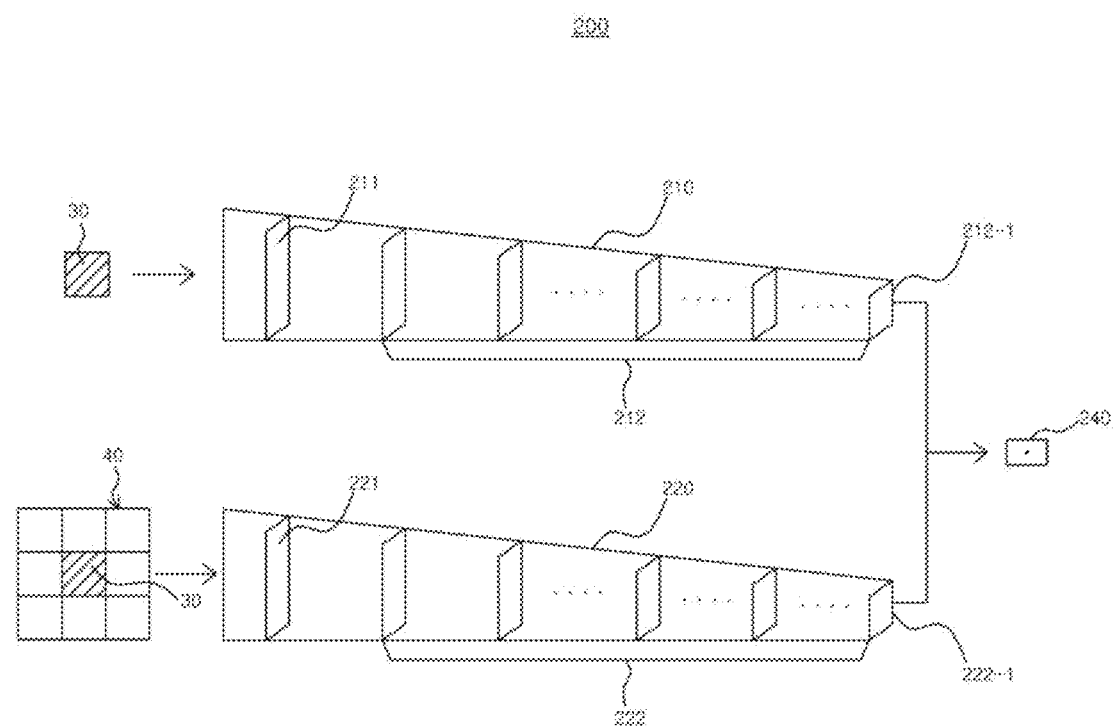

FIGS. 5a and 5b are schematic views showing the configuration of the patch-level classification neural network 200 according to the present invention.

Referring to FIGS. 5a and 5b, the patch-level classification neural network 200 according to the technical features of the present invention includes a micro neural network and a macro neural network.

Referring first to FIG. 5a, as disclosed in the Prior art, the micro neural network includes a plurality of layers 210 and an output layer 230. The plurality of layers 210 include an input layer 211 and a plurality of hidden layers 212.

The macro neural network includes a plurality of layers 220 and the output layer 230. The plurality of layers 220 include an input layer 221 and a plurality of hidden layers 222.

The micro neural network receives a specific patch 30 as an input and produces output data defined by the diagnosis result of the specific patch, that is, the output layer 230.

Further, the macro neural network receives a macro patch 40 including the specific patch 30 and at least one or more patches adjacent to the specific patch 30 as an input and produces the diagnosis result of the specific patch.

That is, the patch-level classification neural network 200 according to the technical features of the present invention can produce the diagnosis result of the specific patch 30 in consideration of the image features of the specific patch 30 and the image features of the patches adjacent to the specific patch 30.

In FIGS. 5a and 5b, an example in which 3×3 patches surrounding the specific patch are provided as the macro patch 40, and of course, various examples may be provided.

The output layer 230 receives the output data of a first previous layer 212-1 as a previous layer thereto, which is included in the micro neural network, and the output data of a second previous layer 222-1 as a previous layer thereto, which is included in the macro neural network, and produces the output data defined by the output layer 230. The first previous layer 212-1, the second previous layer 222-1, and the output layer 230 are fully connected.

As the feedforward function for defining the output layer 230, any one of various functions for producing the output data to the output layer 230 as the result of the input data to the input layer may be used.

So as to perform the diagnosis for the specific patch 30, accordingly, the patch-level classification neural network 200 learns to produce the output data of the output layer 230, which correspond to annotation values of training data, in consideration of the image features of the specific patch 30 and the image features of the macro patch 40 including the specific patch 30.

That is, the training data are used to allow the patch-level classification neural network 200 to learn, and the training data may include a pair of specific patch 30 and macro patch 40. Further, the macro patch 40 learns using the annotation information of the specific patch 30.

Accordingly, the patch-level classification neural network 200 learns to produce the output data corresponding to the annotation information of the specific patch 30 in consideration of both of the image features of the specific patch 30 and the image features of the macro patch 40.

If the neural network 200 with the learning receives the subject patch as the diagnosis subject and the macro patch corresponding to the subject patch as the input data of the input layers of the micro neural network and the macro neural network, respectively, the neural network 200 produces the diagnosis result of the subject patch, that is, the output data of the output layer 230.

As shown in FIG. 5a, the output layer 230 produces the diagnosis result for the specific patch 30 as the diagnosis subject, as the output data. The diagnosis result includes at least state information of the disease of the specific patch 30. The state information of the disease indicates whether the specific disease is simply expressed on the specific patch 30 (or it means a probability value). However, the state information of the disease may further include the information of the progression of the disease according to the types of diseases.

The output layer is designed to produce both of the output data simply indicating whether the disease is expressed and additional information, as disclosed in the Prior art. For example, the output layer is designed to produce the information of the progression of the disease and/or the expression degrees of associated factors with the values of the state channels. The related techniques are disclosed in detail in the Prior art, and a detailed explanation for them will be avoided for the brevity of the description.

If the neural network 200 as shown in FIG. 5a is used, of course, a layer, which receives the output data of the output layer 230 to produce the feature value of the disease expression probability of the finally received patch, may be further provided, which is not shown in FIG. 5a.

Further, as shown in FIG. 5b, the patch-level classification neural network 200 is designed to have a layer 240 adapted to produce the feature value of the disease expression probability of the finally received patch, which is provided by replacing the layer, as shown in FIG. 5a, for producing the state channels and the associated factor channels.

According to another embodiment of the present invention, the patch-level classification neural network 200 may be designed to have a single path, not two paths (the micro neural network and the macro neural network) as shown in FIG. 5a. Such an example is given as shown in FIG. 6.

FIG. 6 is a schematic view showing another example in the configuration of the patch-level classification neural network 200 according to the present invention.

Referring to FIG. 6, the patch-level classification neural network 200 receives the inputs in the unit of patch and determines whether the disease is expressed on the input patches. In this case, as shown, the neural network receives four channel (for example, RGB and gray channels) data as the inputs.

As shown in FIG. 6, the received data pass through a plurality of layers such as a convolution layer and a max polling layer and produces the output data indicating whether the input patches are disease patches. The neural network may be provided as the neural network using a known DenseNet model. In this case, the neural network according to the technical features of the present invention has a 1×1 convolution more added when compared to the DenseNet model, so that internal feature maps can be effectively checked through the 1×1 convolution. Further, a sigmoid function is used as an activation function, but of course, various activation functions may be used.

Of course, the neural network for performing the patch-level diagnosis through other various methods may be defined, which will be easily derived by a person having ordinary skill in the art.

Figure 7:
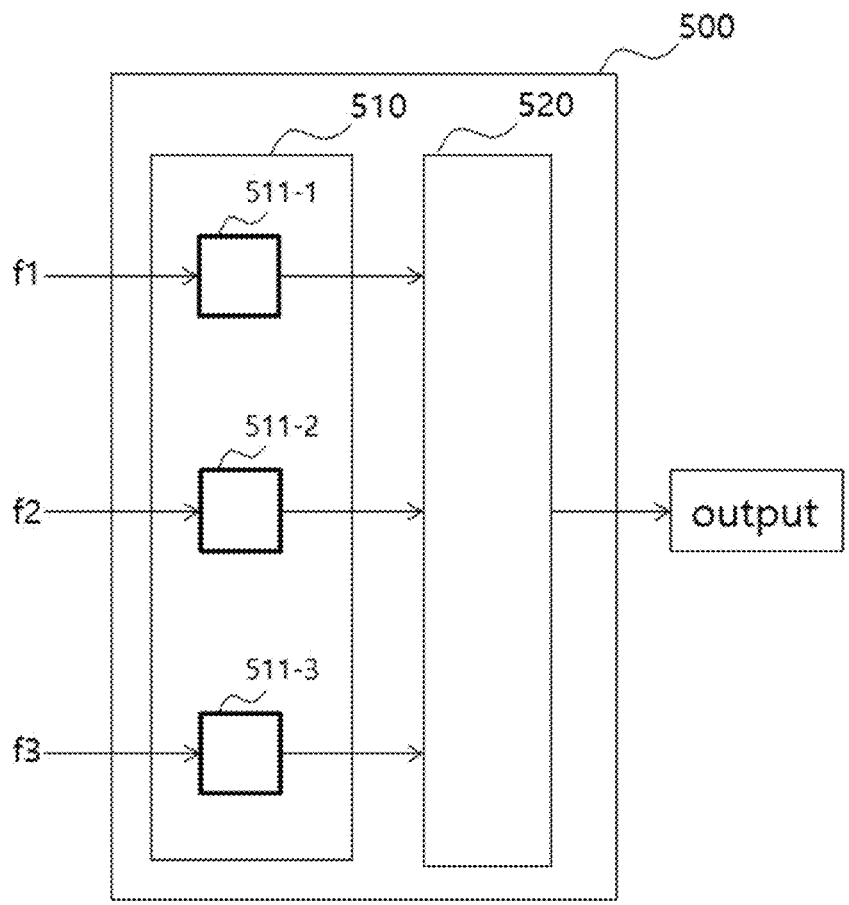
FIG. 7 is a block diagram showing an overall configuration of a patch-level segmentation architecture according to the present invention.

FIG. 7 is a block diagram showing an overall configuration of the patch-level segmentation architecture 500 according to the present invention.

Referring to FIG. 7, the patch-level segmentation architecture 500 includes a non-local correlation calculation sub-architecture 510 and a segmentation sub-architecture 520.

As mentioned above, the feature maps f1, f2, and f3 are produced by the respective feature map extraction layers in the process of the classification performed by the patch-level classification neural network 200, and the feature maps are inputted to non-local correlation calculation nodes 511-1 to 511-3 included in the non-local correlation calculation sub-architecture 510, respectively.

The respective non-local correlation calculation nodes 511-1 to 511-3 correspond to the two or more feature map extraction layers included in the patch-level classification neural network 200, and accordingly, they perform non-local correlation calculation processes for the feature maps f1, f2, and f3 received from the feature map extraction layers corresponding thereto.

The non-local correlation calculation processes performed by the respective non-local correlation calculation nodes 511-1 to 511-3 include convolution, non-local block, or a parallel process of convolution and non-local block.

Accordingly, the respective non-local correlation calculation nodes 511-1 to 511-3 perform one or more convolution or non-local block processes or the parallel processes of the convolution and non-local block, thereby producing one result or two or more results.

According to embodiments of the present invention, the convolution performed by at least a portion of the respective non-local correlation calculation nodes 511-1 to 511-3 may be dilated convolution (which is also called "atrous convolution"). Unlike the typical convolution, the dilated convolution is performed with predetermined rates between adjacent pixels, while not extracting the features from the adjacent pixels. For example, any one (for example, 511-2) of the non-local correlation calculation nodes 511-1 to 511-3 performs 1×1 dilated convolution, 3×3 dilated convolution with a rate of 6, 3×3 dilated convolution with a rate of 12, and 3×3 dilated convolution with a rate of 18, thereby producing four convolution results (features).

Further, the non-local block performed by at least a portion of the respective non-local correlation calculation nodes 511-1 to 511-3 may indicate the operation used to calculate non-local correlation of the feature maps, and a detailed explanation of the non-local block is disclosed in paper introduced by Kaiming He et al in "Non-local Neural Networks" (https://arxiv.org/pdf/1711.07971.pdf).

According to embodiments of the present invention, further, at least a portion of the respective non-local correlation calculation nodes 511-1 to 511-3 performs upscaling (for example, upsampling) or downscaling (for example, downsampling) for the results after performing the non-local correlation calculation processes.

Further, the segmentation sub-architecture 520 specifies the disease areas of the patches, based on the convolution results produced from the non-local correlation calculation sub-architecture 510.

The segmentation sub-architecture 520 performs given operations for the convolution results produced from the non-local correlation calculation sub-architecture 510. The operations of the segmentation sub-architecture 520 are defined by a combination of concatenation and/or convolution. According to embodiments of the present invention, the concatenation and the convolution may be combined in various methods.

Figure 8A:
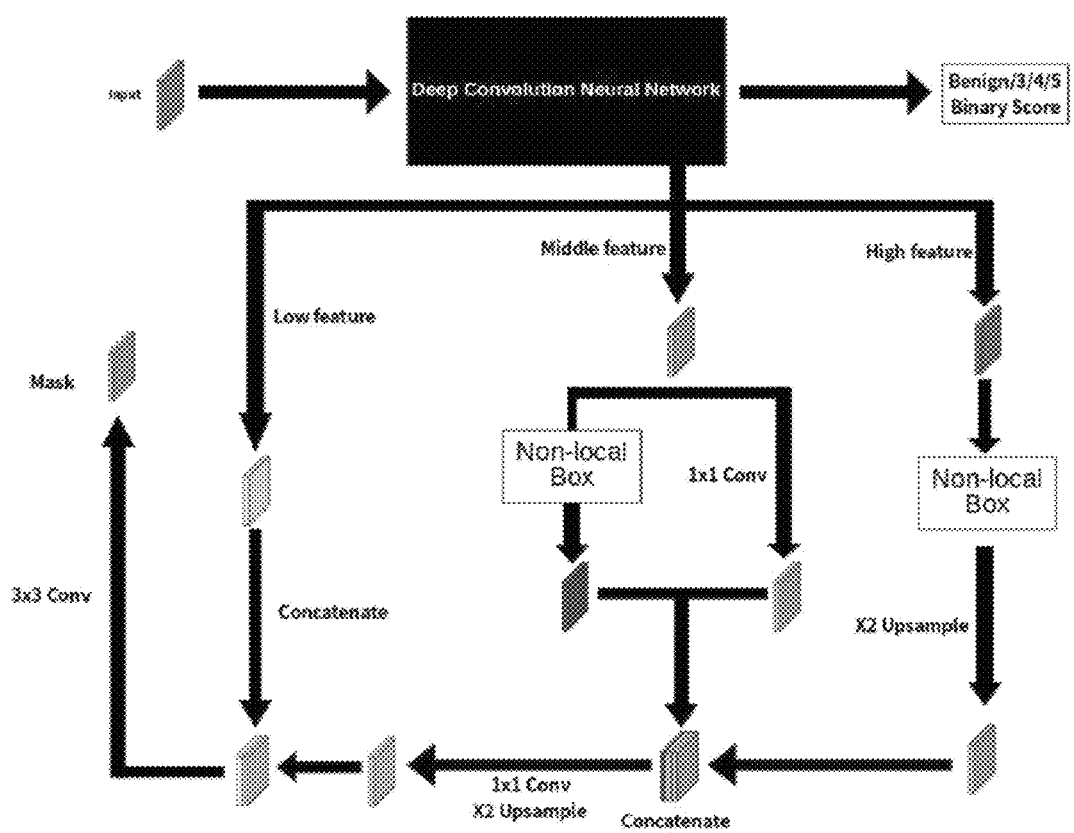
FIG. 8a is a diagram showing a specific example of the patch-level classification neural network according to the present invention.
Figure 8B:
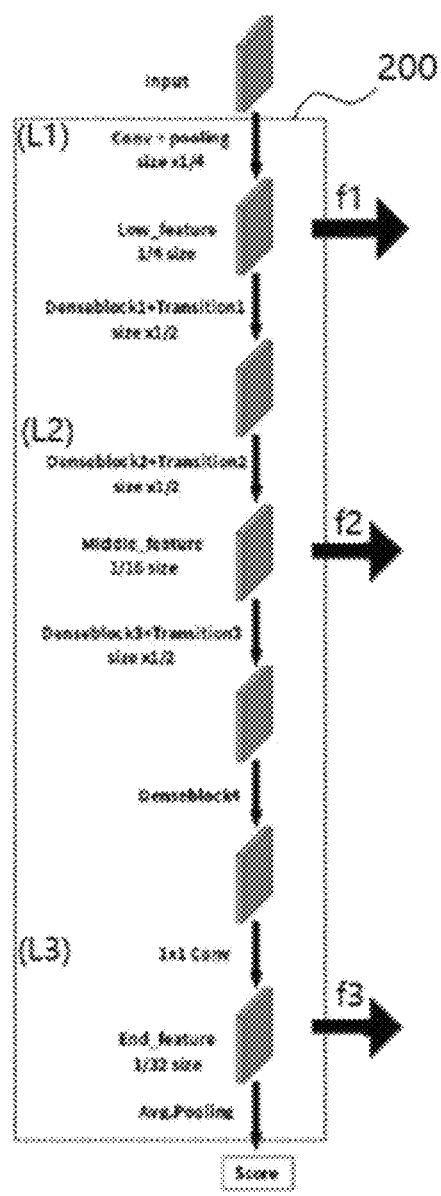

FIG. 8a is a diagram showing a specific example of the patch-level classification neural network 400 according to the present invention, and FIG. 8b is a diagram showing an example of a deep neural network (that is, the patch-level classification neural network 200) of FIG. 8a.

Referring first to FIG. 8b, the patch-level classification neural network 200, which is included in the patch-level segmentation neural network, performs classification. To perform the classification, the patch-level classification neural network 200 receives the patches from the input layer and produces the low feature f1 having a size of ¼ from the first feature map extraction layer L1 through convolution and pooling operation. Next, the patch-level classification neural network 200 produces a middle feature f2 having a size of ¹⁄₁₆ from the second feature map extraction layer L2 through a second dense block and a second transition operation. After that, the patch-level classification neural network 200 produces a high (end) feature f3 having a size of ¹⁄₁₆ from the third feature map extraction layer L3 through a third dense block, a third transition operation, a fourth dense block, and 1×1 convolution, sequentially. After that, the patch-level classification neural network 200 produces the scores indicating whether the disease is expressed through average pulling.

As shown in FIG. 8a, further, the patch-level segmentation architecture 500 performs the segmentation using the respective features produced from the patch-level classification neural network 200.

In specific, the respective non-local correlation calculation nodes 511-1 to 511-3, which are included in the non-local correlation calculation sub-architecture 510, perform the predetermined correlation calculation processes for the feature maps received from the feature map extraction layers corresponding thereto.

The correlation calculation processes performed by the respective nodes are convolution, non-local block, or a parallel process of convolution and non-local block.

In the example as shown in FIG. 8b, the low-level non-local correlation calculation node 511-1 performs the 1×1 convolution for the low feature map f1 received from the first feature map extraction layer L1 corresponding thereto and produces a first convolution result.

Further, the middle-level non-local correlation calculation node 511-2 performs the non-local block and convolution processes in parallel for the middle feature map f2 received from the second feature map extraction layer L2 corresponding thereto and produces a first non-local result and a second convolution result.

The high-level non-local correlation calculation node 511-3 performs the non-local block for the high feature map f3 received from the third feature map extraction layer L3 corresponding thereto and produces a second non-local result.

Further, the segmentation sub-architecture 520 receives the results produced from the non-local correlation calculation sub-architecture 510 and performs predetermined operations. In an example as shown in FIG. 8a, the segmentation sub-architecture 520 concatenates the first non-local result 1 and the second convolution result 2 produced from the middle-level non-local correlation calculation node 511-2 and the upscaling result 3 of the second non-local block produced from the high-level non-local correlation calculation node 511-3 to thus produce a first middle result 4, concatenates a second middle result 5 produced by convoluting and upscaling the first middle result 4 and the first convolution result to thus produce a third middle result 6, and performs the convolution for the third middle result 6 to produce a mask 7 corresponding to the disease area of the patch.

With the use of the neural network according to the technical features of the present invention, accordingly, a tangential issue can be substantially removed and the accuracy of segmentation can be greatly enhanced. So as to enhance the accuracy of segmentation in a typical neural network, features have to be extracted well from the input data, and after an initial weight value of the neural network before training is set well, the training has to be conducted, which are well known empirically. However, as mentioned above, the segmentation according to the technical features of the present invention is performed by the patch-level classification neural network-based neural network combined with the segmentation architecture having the specific structure, and the features extracted in the patch-level classification process have the characteristics of the input data well. Accordingly, the features are still used even in the segmentation process, thereby enhancing the accuracy of the segmentation.

Further, the neural networks as shown in FIGS. 8a and 8b are just examples for implementing the technical features of the present invention, and accordingly, the patch-level classification neural network and the patch-level segmentation architecture having various structures may be provided.

Referring back to FIG. 3, the diagnosis module 120 may include the slide diagnosis engine, and the slide diagnosis engine learns through the control module 110 and is thus implemented.

The slide diagnosis engine may mark the diseased patches according to the output results of the neural network. In this case, marking means that the diseased patches are distinguished from other patches in the slide. For example, the slide diagnosis engine marks the diseased patches to allow them to be distinguished from other patches and thus produces heat maps. Based on the produced heat maps, the diseased patches can be clustered to a plurality of clusters. According to the present invention, the slide diagnosis engine allows the diseased patches to be clustered to at least two or more clusters. Among them, the two largest clusters can be used for the slide diagnosis. However, of course, two or more clusters can be used for the slide diagnosis.

The slide diagnosis engine calculates given feature values by cluster. The slide diagnosis engine learns to produce an output indicating whether the disease is expressed on the slide corresponding to the calculated feature values, that is, the input data.

Further, the slide diagnosis engine learns in consideration of all of the thresholds. As a result, the slide diagnosis engine produces a slide diagnosis result robust to threshold setting, which will be discussed later.

The pre-processing module 130 performs the pre-processing for the bio-image, which is required before the diagnosis is performed using the neural network. For example, the pre-processing for the bio-image includes a process of making the bio-image to the form of patches with a predetermined size, and as mentioned above, the pre-processing calculates the gray values of the pixels by patch. If necessary, further, the pre-processing performs appropriate image processing for the neural network, which will be easily understood by a person having ordinary skill in the art.

Figure 9:
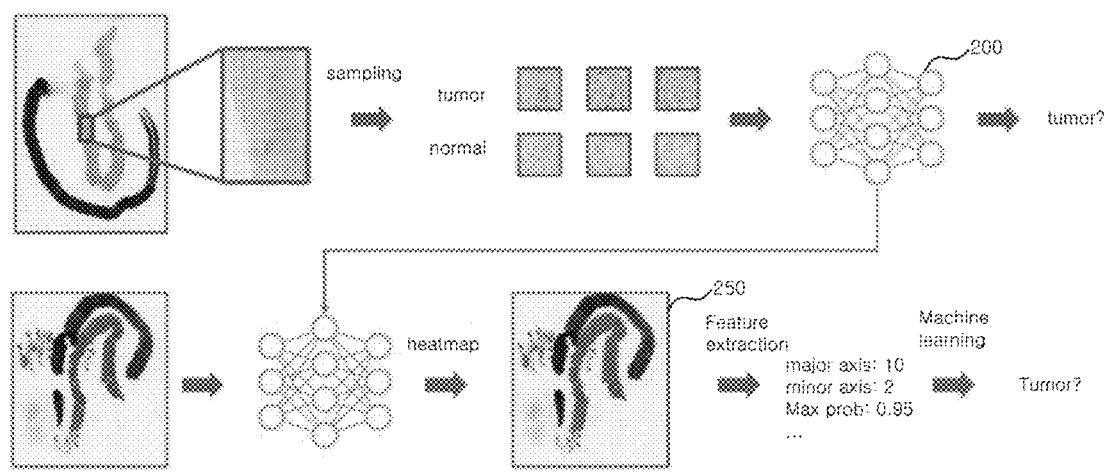
FIG. 9 is a concept view showing a two-phase disease diagnosis method according to the present invention.

FIG. 9 is a concept view showing a two-phase disease diagnosis method according to the present invention.

As shown in FIG. 9, the sampled patches from the bio-image corresponding to the biological tissue, that is, the slide can be used in learning the neural network. The patches are labeled with cancer and normal, and they are sampled to a given ratio with respect to each other.

As mentioned above, the neural network 200 learns to receive the input data by patch that further include the gray channel and produce output data indicating whether the patches have a cancer (or indicating probability values).

As shown in a lower portion of FIG. 9, if the slide is received, the neural network 200 after the learning performs the patch-level diagnosis for the respective patches included in the slide.

Further, the slide diagnosis engine marks the disease patches according to the patch-level diagnosis results. For example, the heat maps as shown in FIG. 9 are produced.

Figure 10A:
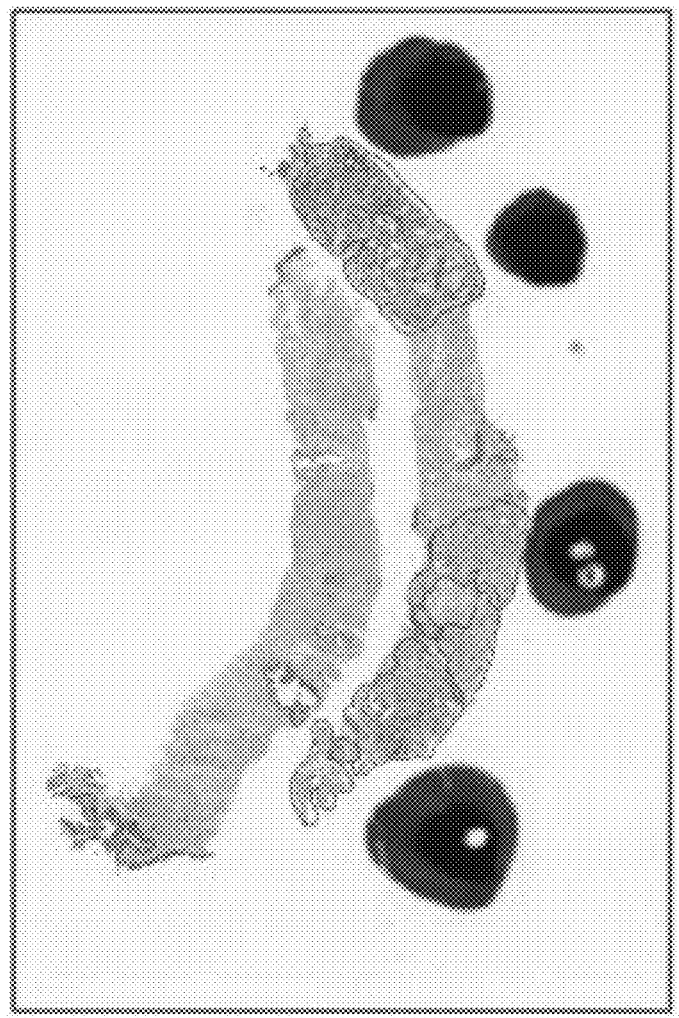
FIGS. 10a and 10b are views showing marking results obtained by patch-level diagnosis results according to the present invention.
Figure 10B:
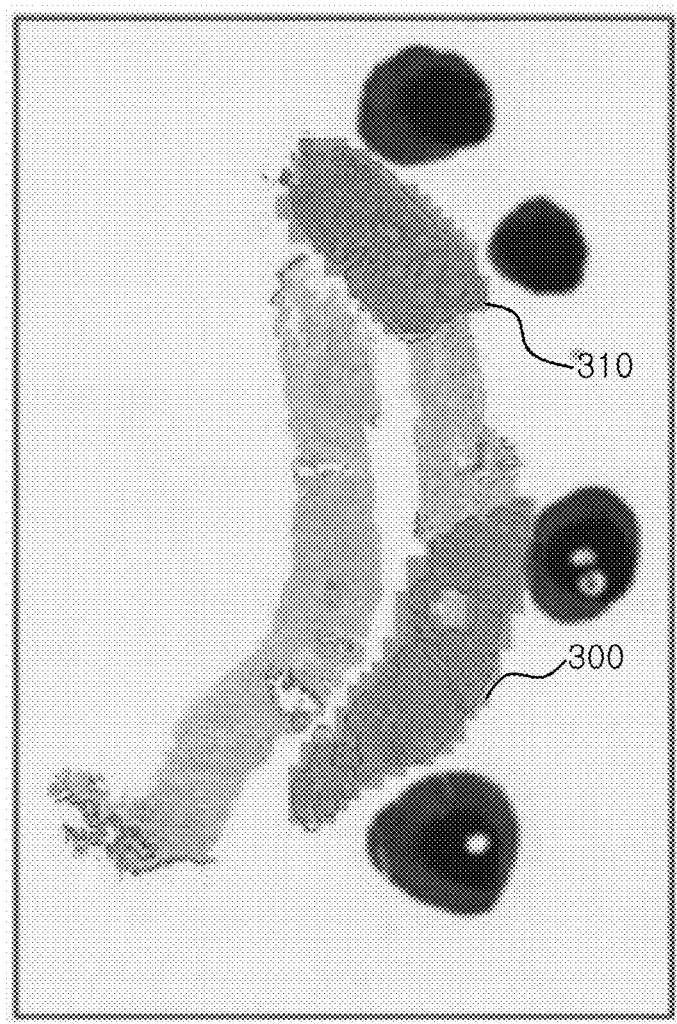

FIGS. 10a and 10b are views showing marking results obtained by the patch-level diagnosis results according to the present invention. FIG. 10a indicates the images of the biological tissue labeled by a skilled person, and FIG. 10b indicates the heat maps produced by the neural network 200. As shown in FIGS. 10a and 10b, it can be appreciated that the diagnoses can be very accurately performed.

Further, the slide diagnosis engine produces clusters in accordance with the produced heat maps. The slide diagnosis engine can cluster the disease patches using a given clustering algorithm. According to the present invention, the slide diagnosis engine performs the clustering through a known DB SCAN algorithm, but of course, various clustering techniques may be used.

The slide diagnosis engine extracts cluster features according to the clusters produced as the clustering result.

The cluster features are characteristic values indicating the characteristics associated with the expression of the disease.

For example, the cluster features include the number of disease patches included in the clusters, an average value of disease probability values by patch, a maximum value of disease probability values by patch, and a minimum value of disease probability values by patch. If the cluster features are included, it can be checked that the accuracy of the diagnosis result of the slide diagnosis engine is relatively high.

According to the present invention, further, the cluster features may further include a major axis, a minor axis, an area, and a density for each cluster. They have close relation with the physical features of the clusters, and if such cluster features are additionally used, diagnosis performance may be more enhanced.

Further, the position, size, and features of the cluster may be varied, depending on whether the patches of the cluster are determined as the disease patches. Further, they are dependent upon whether which threshold is used in the patch-level diagnosis.

According to the technical features of the present invention, the plurality of thresholds are used for the slide-level diagnosis.

According to the present invention, for example, five different thresholds are used, but of course, the number of thresholds may be freely set.

The diagnosis result of the specific patch, through which the specific patch is determined as the disease patch, may be varied according to the thresholds, and accordingly, the clustering may be of course varied.

According to the present invention, the slide diagnosis engine clusters the patches on which the disease is expressed with respect to N (for example, five) thresholds according to a given method to thus produce M (for example, two) clusters.

Next, P (for example, eight) cluster features for each cluster are calculated. In this case, M×N×P (for example, 80) cluster features for one slide can be extracted.

The slide diagnosis engine learns to receive the feature values as input values and produce the output data indicating whether the disease exists on the slide.

In the description, further, an example in which the technical features of the present invention are applied to the prostate cancer is given, but if the technical features of the present invention are applied even to other diseases having a need to perform the diagnosis for a specific tissue in consideration of the specific tissue and the adjacent tissues to the specific tissue, the diagnosis result can be accurately obtained, which will be easily understood by a person having ordinary skill in the art.

According to embodiments of the present invention, further, the diagnosis system 100 may include a processor and a memory for recording a program executed by the processor. The processor may include a single core CPU or multi-core CPU. The memory may include a high speed random access memory, one or more magnetic disc storage devices, a flash memory, or a non-volatile memory such as a non-volatile solid state memory. Access to the memory through the processor and other components is controlled by means of a memory controller.

Further, a diagnosis method according to the present invention may be implemented in the form of a program instruction that can be performed through computers, and may be recorded in a computer readable recording medium. According to the present invention, further, a control program and a subject program may be recorded in a computer readable recording medium. The computer readable recording medium may include all kinds of recording devices in which data readable by a computer system are recorded.

The program instruction recorded in the recording medium is specially designed and constructed for the present invention, but may be well known to and may be used by those skilled in the art of computer software.

The computer readable recording medium may include a magnetic medium such as a hard disc, a floppy disc, and a magnetic tape, an optical recording medium such as a compact disc read only memory (CD-ROM) and a digital versatile disc (DVD), a magneto-optical medium such as a floptical disk, and a hardware device specifically configured to store and execute program instructions, such as a read only memory (ROM), a random access memory (RAM), and a flash memory. Further, the computer readable recording medium is distributed over network-coupled computer systems so that computer readable codes are stored and executed in a distributed fashion.

Further, the program command may include a machine language code generated by a compiler and a high-level language code executable by a device for electronically processing information, for example, a computer through an interpreter and the like.

The hardware device may be configured to operate as one or more software modules in order to perform operations of the present invention, and vice versa.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. For example, each component explained in a single form may be provided in a distributed form, and contrarily, each component explained in a distributed form may be provided in a coupled form.

The embodiments of the present invention have been disclosed in the specification and drawings. In the description of the present invention, special terms are used not to limit the present invention and the scope of the present invention as defined in claims, but just to explain the present invention. Therefore, persons skilled in the relevant art can appreciate that many modifications and variations are possible in light of the above teachings. It is therefore intended that the scope of the invention be limited not by this detailed description, but rather by the claims appended hereto.

The present invention is applicable to a disease diagnosis system and method for performing segmentation using a neural network and a non-local block.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A disease diagnosis system implemented in a system having a processor and a storage device storing a neural network to perform a disease diagnosis using a slide as a bio-image and the neural network, the disease diagnosis system comprising:
   a patch-level segmentation neural network for receiving, given patches made by dividing the slide into a predetermined size, as input layers, to specify a disease area in which a given disease exists among the patches,
   wherein the patch-level segmentation neural network comprises:
   a patch-level classification neural network for receiving the patches as the input layers to produce a patch-level classification result indicating whether the disease exists on the patches; and
   a patch-level segmentation architecture for receiving feature maps produced from two or more feature map extraction layers among hidden layers included in the patch-level classification neural network to thus specify the disease area among the patches, and
   the patch-level segmentation architecture comprises:
   a non-local correlation calculation sub-architecture having non-local correlation calculation nodes corresponding to the two or more feature map extraction layers, respectively, the non-local correlation calculation nodes performing non-local correlation calculation processes for the feature maps received from the feature map extraction layers corresponding thereto, the correlation calculation processes being performed by convolution, non-local block, or a parallel process of convolution and non-local block; and
   a segmentation sub-architecture for specifying the disease area among the patches, based on the results produced from the non-local correlation calculation sub-architecture.

2. The disease diagnosis system according to claim 1, wherein the segmentation sub-architecture produces a mask corresponding to the disease area among the patches through convolution and concatenation for the results produced from the non-local correlation calculation sub-architecture.

3. The disease diagnosis system according to claim 1, wherein the feature map extraction layers of the patch-level classification neural network comprise a low feature map extraction layer, a middle feature map extraction layer, and a high feature map extraction layer, and the non-local correlation calculation nodes of the non-local correlation calculation sub-architecture comprise a low-level non-local correlation calculation node for performing the convolution process for the feature map received from the low feature map extraction layer to produce a first convolution result, a middle-level non-local correlation calculation node for performing the non-local block and convolution processes in parallel for the feature map received from the middle feature map extraction layer to produce a first non-local result and a second convolution result, and a high-level non-local correlation calculation node for performing the non-local block for the feature map received from the high feature map extraction layer to produce a second non-local result.

4. The disease diagnosis system according to claim 3, wherein the segmentation sub-architecture concatenates the first non-local result, the second convolution result, and an upscaling result of the second non-local block to thus produce a first middle result, concatenates a second middle result produced by convoluting and upscaling the first middle result and the first convolution result to thus produce a third middle result, and performs the convolution for the third middle result to produce the mask corresponding to the disease area among the patches.

5. The disease diagnosis system according to claim 1, further comprising a slide diagnosis engine for marking the patches classified as disease patches according to the patch level classification results for the patches of the slide to thus produce a slide-level diagnosis result indicting whether the disease exists on the slide according to the marking results.

6. The disease diagnosis system according to claim 1, wherein the slide is a biological tissue image.

7. A disease diagnosis method conducted in a system having a processor and a storage device storing a neural network to perform a disease diagnosis using a slide as a bio-image and the neural network, the disease diagnosis method comprising the step of:
receiving, given patches made by dividing the slide into a predetermined size, as input layers, to specify a disease area in which a given disease exists among the patches, through a patch-level segmentation neural network,
wherein the patch-level segmentation neural network comprises:
a patch-level classification neural network for receiving the patches as the input layers to produce a patch-level classification result indicating whether the disease exists on the patches; and
a patch-level segmentation architecture for receiving feature maps produced from two or more feature map extraction layers among hidden layers included in the patch-level classification neural network to thus specify the disease area among the patches, and
the patch-level segmentation architecture comprises:
a non-local correlation calculation sub-architecture having non-local correlation calculation nodes corresponding to the two or more feature map extraction layers, respectively, the non-local correlation calculation nodes performing non-local correlation calculation processes for the feature maps received from the feature map extraction layers corresponding thereto, the correlation calculation processes being performed by convolution, non-local block, or a parallel process of convolution and non-local block; and
a segmentation sub-architecture for specifying the disease area among the patches, based on the results produced from the non-local correlation calculation sub-architecture.

8. The disease diagnosis method according to claim 7, wherein the segmentation sub-architecture produces a mask corresponding to the disease area among the patches through convolution and concatenation for the results produced from the non-local correlation calculation sub-architecture.

9. The disease diagnosis method according to claim 7, wherein the feature map extraction layers of the patch-level classification neural network comprise a low feature map extraction layer, a middle feature map extraction layer, and a high feature map extraction layer, and the non-local correlation calculation nodes of the non-local correlation calculation sub-architecture comprise a low-level non-local correlation calculation node for performing the convolution process for the feature map received from the low feature map extraction layer to produce a first convolution result, a middle-level non-local correlation calculation node for performing the non-local block and convolution processes in parallel for the feature map received from the middle feature map extraction layer to produce a first non-local result and a second convolution result, and a high-level non-local correlation calculation node for performing the non-local block for the feature map received from the high feature map extraction layer to produce a second non-local result.

10. The disease diagnosis method according to claim 9, wherein the segmentation sub-architecture concatenates the first non-local result, the second convolution result, and an upscaling result of the second non-local block to thus produce a first middle result, concatenates a second middle result produced by convoluting and upscaling the first middle result and the first convolution result to thus produce a third middle result, and performs the convolution for the third middle result to produce the mask corresponding to the disease area among the patches.

11. The disease diagnosis method according to claim 7, further comprising the step of: marking the patches classified as disease patches according to the patch level classification results for the patches of the slide to thus produce a slide-level diagnosis result indicting whether the disease exists on the slide according to the marking results, through the disease diagnosis system.

12. A computer program installed in a data processing device and recorded in a medium, wherein the medium does not constitute a transitory data signal, for implementing the method according to any one of claims 7 to 10.

* * * * *